United States Patent
Palle et al.

(10) Patent No.: US 7,238,700 B2
(45) Date of Patent: *Jul. 3, 2007

(54) $A_{2B}$ ADENOSINE RECEPTOR ANTAGONISTS

(75) Inventors: Venkata Palle, Gurgaon (IN); Vaibhav Varkhedkar, San Diego, CA (US); Jeff Zablocki, Mountain View, CA (US); Dengming Xiao, Longmont, CO (US)

(73) Assignee: CV Therapeutics, Inc., Palo Alto, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/837,290

(22) Filed: Apr. 30, 2004

(65) Prior Publication Data
US 2004/0209899 A1    Oct. 21, 2004

Related U.S. Application Data

(63) Continuation of application No. 10/184,494, filed on Jun. 27, 2002, now Pat. No. 6,770,651.

(60) Provisional application No. 60/302,208, filed on Jun. 29, 2001.

(51) Int. Cl.
| | | |
|---|---|---|
| C07D 473/16 | (2006.01) | |
| C07D 473/24 | (2006.01) | |
| C07D 473/18 | (2006.01) | |
| A61K 31/52 | (2006.01) | |
| A61K 31/522 | (2006.01) | |

(52) U.S. Cl. .............. 514/263.4; 514/263.38; 514/263.37; 544/276; 544/277

(58) Field of Classification Search ............ None
See application file for complete search history.

(56) References Cited

U.S. PATENT DOCUMENTS

| | | | | |
|---|---|---|---|---|
| 2003/0149060 A1* | 8/2003 | Cristalli | ................. | 514/263.23 |
| 2004/0048868 A1* | 3/2004 | Edwards et al. | ............ | 514/249 |
| 2004/0204428 A1* | 10/2004 | Giorgio et al. | .......... | 514/263.2 |

* cited by examiner

*Primary Examiner*—Mark L. Berch
(74) *Attorney, Agent, or Firm*—Brian Lewis; J. Elin Hartrum; CV Therapeutics, Inc.

(57) ABSTRACT

Disclosed are novel $A_{2B}$ adenosine receptor antagonists of Formula I:

A compound of the formula:

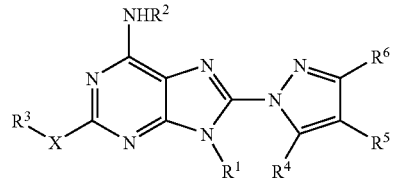

Formula I wherein:

$R^1$ is optionally substituted alkyl or a group —Y-Z, in which Y is a covalent bond or optionally substituted alkylene, and Z is optionally substituted cycloalkyl, optionally substituted aryl, optionally substituted heteroaryl, optionally substituted heterocyclyl, optionally substituted alkenyl or optionally substituted alkynyl, with the proviso that when Y is a covalent bond Z cannot be alkenyl or alkynyl; and X is oxygen, sulfur, or NH—, or a pharmaceutically acceptable salt, ester, or prodrug thereof. The compounds are particularly useful for treating asthma and diabetic retinopathy.

38 Claims, No Drawings

$A_{2B}$ ADENOSINE RECEPTOR ANTAGONISTS

This Patent Application is a continuation of U.S. patent application Ser. No. 10/184,494, filed Jun. 27, 2002, now issued as U.S. Pat. No. 6,770,651 which claims the benefit under 35 U.S.C. 119(e) of U.S. Provisional Application Ser. No. 60/302,208, filed Jun. 29, 2001, the entire disclosure of which are herein incorporated by reference.

FIELD OF THE INVENTION

The present invention relates to novel compounds that are $A_{2B}$ adenosine receptor antagonists, and to their use in treating mammals for various disease states, such as gastrointestinal disorders, immunological disorders, neurological disorders, and cardiovascular diseases due to both cellular hyperproliferation and apoptosis, and the like. The invention also relates to methods for the preparation of such compounds, and to pharmaceutical compositions containing them.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_1$ adenosine receptor agonists modulate the cardiostimulatory effects of catecholamine, thus slowing the heart rate, and also prolong impulse propagation through the AV node. Thus, stimulation of $A_1$ receptors provides a method of treating supraventricular tachycardias, including termination of nodal re-entrant tachycardias, and control of ventricular rate during atrial fibrillation and flutter. $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153), and $A_3$ adenosine receptors modulate cell proliferation processes.

Adenosine $A_{2B}$ receptors are ubiquitous, and regulate multiple biological activities. For example, adenosine binds to $A_{2B}$ receptors on endothelial cells, thereby stimulating angiogenesis. Adenosine also regulates the growth of smooth muscle cell populations in blood vessels. Adenosine stimulates $A_{2B}$ receptors on mast cells, thus modulating Type I hypersensitivity reactions. Adenosine also stimulates gastrosecretory activity by ligation with $A_{2B}$ in the intestine. Binding of $A_{2B}$ receptors in the brain leads to the release of IL-6, which provides a protective effect to the cerebrum from ischemia While many of these biological effects of adenosine are necessary to maintain normal tissue homeostasis, under certain physiological changes it is desirable to curtail its effects. For example, the binding of $A_{2B}$ receptors stimulates angiogenesis by promoting the growth of endothelial cells. Such activity is necessary in healing wounds, but the hyperproliferation of endothelial cells promotes diabetic retinopathy. Also, an undesirable increase in blood vessels occurs in neoplasia. Accordingly, inhibition of the binding of adensoine to $A_{2B}$ receptors in the endothelium will alleviate or prevent hypervasculation, thus preventing retinopathy and inhibiting tumor formation. Adensosine also plays a role in vascular disease by causing the apoptosis of smooth muscle cells, leading to atherosclerosis and restenosis.

$A_{2B}$ receptors are found in the colon in the basolateral domains of intestinal epithelial cells, and when acted upon by the appropriate ligand act to increase chloride secretion, thus causing diarrhea, which is a common and potentially fatal complication of infectious diseases such as cholera and typhus. $A_{2B}$ antagonists can therefore be used to block intestinal chloride secretion, and are thus useful in the treatment of inflammatory gastrointestinal tract disorders, including diarrhea.

Insensitivity to insulin exacerbates diabetes and obesity. Insulin sensivity is decreased by the interaction of adenosine with $A_{2B}$ receptors. Thus, blocking the adenosine $A_{2B}$ receptors of individuals with diabetes or obesity would benefit patients with these disorders.

Another adverse biological effect of adenosine acting at the $A_{2B}$ receptor is the over-stimulation of cerebral IL-6, a cytokine associated with dementias and Altheimer's disease. Inhibiting the binding of adenosine to $A_{2B}$ to receptors would therefore mitigate those neurological disorders that are produced by IL-6.

Type I hypersensitivtiy disorders, such as asthma, hay fever, and atopic ezcema, are stimulated by binding to $A_{2B}$-receptors of mast cells. Therefore, blocking these adenosine receptors would provide a therapeutic benefit against such disorders.

There are several compounds presently used in the treatment of asthma. For example, theophylline is an effective antiasthmatic agent, even though it is a poor adenosine receptor antagonist. However, considerable plasma levels are needed for it to be effective. Additionally, theophylline has substantial side effects, most of which are due to its CNS action, which provide no beneficial effects in asthma, and to the fact that it non-specifically blocks all adenosine receptor subtypes.

Additionally adenosine treatment, such as inhaled adenosine, provokes bronchoconstriction in asthmatics, but not in the normal population. This process is known to involve mast cell activation, in that it releases mast cell mediators, including histamine, PGD2-β-hexosaminidase and tryptase, and because it can be blocked by specific histamine $H_1$ blockers and chromolyn sodium. Accordingly, there is an intrinsic difference in the way adenosine interacts with mast cells from asthmatics, and thus $A_{2B}$ antagonists are particularly useful in modulating mast cell function or in the activation of human lung cells.

Accordingly, it is desired to provide compounds that are potent $A_{2B}$ antagonists, useful in the treatment of various disease states related to modulation of the $A_{2B}$ receptor, in particular cancer, asthma and diarrhea. Preferably, the compounds would be selective for the $A_{2B}$ receptor, thus avoiding side effects caused by interaction with other adenosine receptors.

SUMMARY OF THE INVENTION

It is an object of this invention to provide $A_{2B}$ receptor antagonists. Accordingly, in a first aspect, the invention relates to compounds of Formula I:

Formula I

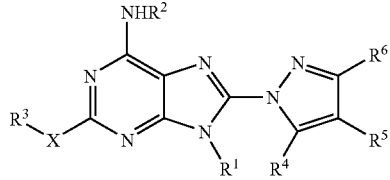

wherein:

$R^1$ is optionally substituted alkyl or a group —Y-Z, in which Y is a covalent bond or optionally substituted alkylene, and Z is optionally substituted cycloalkyl, optionally substituted aryl, optionally substituted heteroaryl, optionally substituted heterocyclyl, optionally substituted alkenyl or optionally substituted alkynyl;

$R^2$ is hydrogen, acyl, optionally substituted alkyl, or a group —Y-Z, in which Y is a covalent bond or optionally substituted alkylene, and Z is optionally substituted cycloalkyl, optionally substituted aryl, optionally substituted heteroaryl, optionally substituted heterocyclyl, optionally substituted alkenyl or optionally substituted alkynyl;

$R^3$ is hydrogen, optionally substituted alkyl or a group —Y-$Z^1$, in which Y is a covalent bond or optionally substituted alkylene, and $Z^1$ is optionally substituted cycloalkyl, optionally substituted aryl, optionally substituted heteroaryl, optionally substituted heterocyclyl, optionally substituted amino, optionally substituted alkenyl or optionally substituted alkynyl, with the proviso that when Y is a covalent bond Z cannot be optionally substituted amino;

$R^4$ and $R^6$ are independently hydrogen, optionally substituted alkyl, optionally substituted aryl, optionally substituted heteroaryl, or optionally substituted heterocyclyl;

$R^5$ is hydrogen, optionally substituted alkyl, halo, $CF_3$, nitro, cyano, optionally substituted alkoxy, optionally substituted thioalkoxy, optionally substituted amino, optionally substituted sulfoxide, optionally substituted sulfone, optionally substituted sulfonamide, optionally substituted acylamino, optionally substituted alkenyl, optionally substituted alkynyl, optionally substituted aryl, optionally substituted heteroaryl, or optionally substituted heterocyclyl; and X is oxygen, sulfur, or —NH—;

with the proviso that when Y is a covalent bond and Z or $Z^1$ is alkenyl or alkynyl, the double bond of the alkenyl or the triple bond of the alkynyl is located at least two carbon atoms away from the attachment to the nitrogen.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with an $A_{2B}$ receptor antagonist, comprising administering to a mammal in need thereof a therapeutically effective dose of a compound of Formula I. Such diseases include, but are not limited to, inflammatory gastrointestinal tract disorders, including diarrhea, cardiovascular diseases, such as atherosclerosis, neurological disorders such as senile dementia, Alzheimer's disease, and Parkinson's disease, diseases related to unwanted angiogenesis, for example diabetic retinopathy and cancer, and asthma.

One preferred class includes those compounds of Formula I in which X is —NH—, particularly those in which $R^1$ is optionally substituted alkyl and $R^2$ is hydrogen, alkyl or acyl. Of these compounds, more preferred are those in which $R^1$ is optionally substituted alkyl, $R^2$ is hydrogen, and $R^3$ is —Y-$Z^1$, in which Y is optionally substituted alkylene and $Z^1$ is optionally substituted aryl, and $R^4$, $R^5$ and $R^6$ are hydrogen, halogen, optionally substituted alkyl or optionally substituted alkenyl. Even more preferred are those in which $R^1$ is lower alkyl or 1-3 carbon atoms, particularly ethyl or n-propyl, Y is lower alkylene of 1-3 carbon atoms, particularly methylene or ethylene, and Z is optionally substituted phenyl.

Of these preferred compounds, one preferred subclass are those compounds in which $R^4$ and $R^6$ are hydrogen or methyl, and $R^5$ is hydrogen, optionally substituted phenyl, lower alkyl, or lower alkenyl. Particularly preferred are those in which $R^4$, $R^5$ and $R^6$ are all hydrogen.

Another preferred class are those compounds in which $R^2$ is acyl.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-5 atoms or groups independently chosen from oxygen, sulfur and —$NR_a$—, where $R_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH2-), ethylene (—CH2CH2-), the propylene isomers (e.g., —CH2CH2CH2- and —CH(CH3)CH2-) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2;.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl may be optionally substituted as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, or optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxynitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is ethyl, $R^2$ is hydrogen, $R^3$ is benzyl, $R^4$ and $R^6$ are methyl, $R^5$ is hydrogen, and X is —NH—:

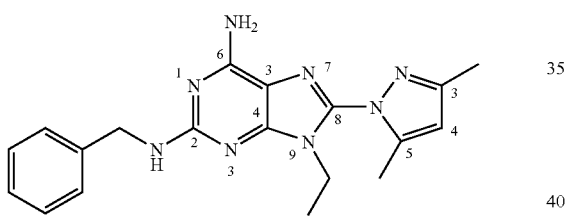

which is named:
$N^2$-benzyl-8-(3,5-dimethylpyrazol-1-yl)-9-ethyl-9H-purine-2,6-diamine.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I may be prepared starting from 2,6-dichloropurine, as shown in Reaction Scheme I.

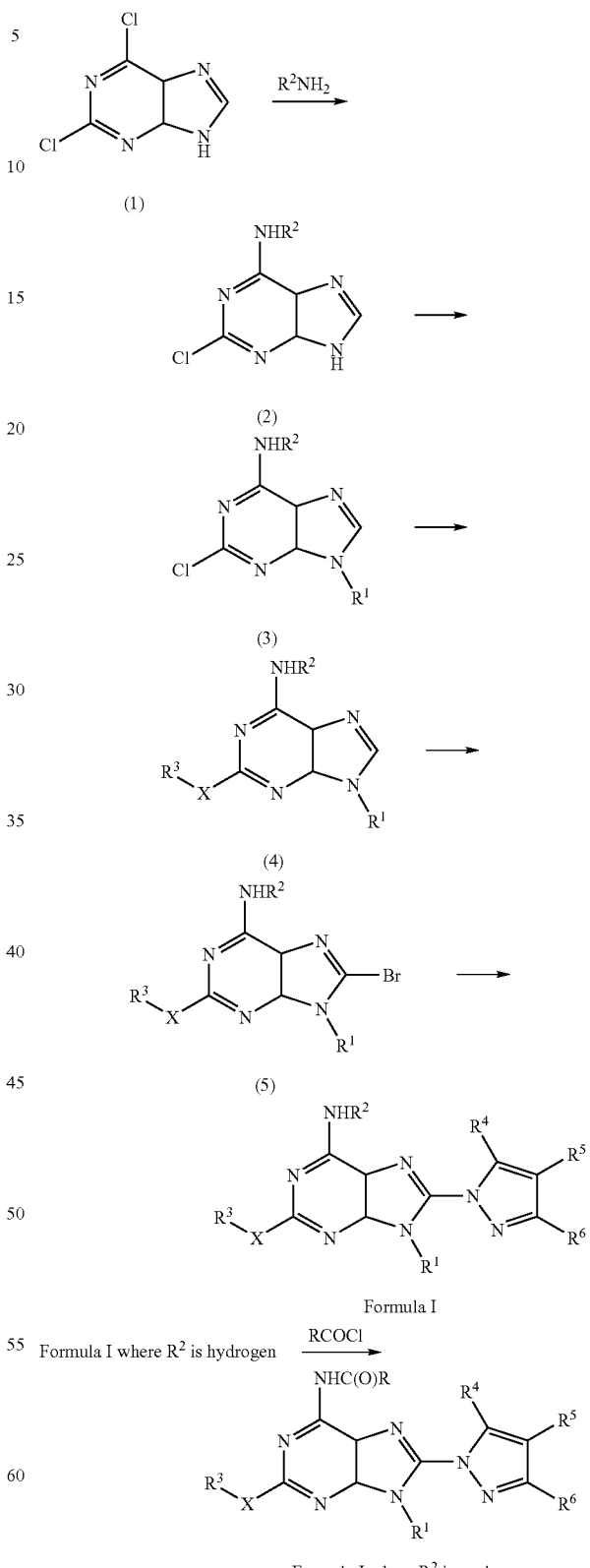

where RC(O)— represents $R^2$ when $R^2$ is acyl.

Step 1—Preparation of Formula (2)

The compound of formula (2) is prepared conventionally from the commercially available compound of formula (1), 2,6-dichloropurine, by reaction with an amine of the formula $R^2NH_2$. For example, where $R^2$ is hydrogen, ammonia is reacted under pressure in a protic solvent, for example methanol, at a temperature of 60–100° C., for about two days. When the reaction is substantially complete, the product of formula (2) is isolated by conventional means, for example removal of the solvent under reduced pressure.

Step 2—Preparation of Formula (3)

The compound of formula (2) is then converted to a compound of formula (3) by alkylation at the 9-position. The compound of formula (2) is reacted with a halide of formula $R^1X$, where $R^1$ is as defined above, with the proviso that it cannot be aryl, and X is chloro, bromo, or iodo, preferably iodo, in the presence of a base, preferably potassium carbonate, in a suitable solvent, preferably acetone. The reaction is preferably conducted at reflux, for about 18 hours. When the reaction is substantially complete, the product of formula (3) is isolated by conventional means, for example removal of the solvent under reduced pressure and slurrying with water before filtering.

Step 3—Preparation of Formula (4)

The 2-chloro moiety is then displaced from the compound of formula (3) by reaction with a compound of formula $R^3XH$ when X is NH, in the presence of a base, or $R^3XM$, where X is oxygen or sulfur and M is an alkali metal. The reaction is carried out in an inert protic solvent, preferably n-butanol, at a temperature of about reflux, for about 24–48 hours. When the reaction is substantially complete, the product of formula (4) is isolated by conventional means, for example by removal of the solvent under reduced pressure, followed by chromatography of the residue on silica gel.

Step 4—Preparation of Formula (5)

The compound of formula (4) is then converted to the 8-bromo derivative of formula (5) by reaction with a suitable brominating agent, for example N-bromosuccinimide. The reaction is carried out in an inert solvent, preferably an ether, more preferably tetrahydrofuran, at about room temperature, for about 1–10 hours, preferably about 2 hours. When the reaction is substantially complete, the product of formula (5) is isolated by conventional means, for example by removal of the solvent under reduced pressure, followed by chromatography of the residue on silica gel.

Step 5—Preparation of Formula I where $R^2$ is Hydrogen

The compound of formula (5) is then converted to a compound of Formula I where $R^2$ is hydrogen by reaction with an optionally substituted pyrazole in the presence of an alkali hydride, preferably sodium hydride. The reaction is carried out in an inert polar solvent, preferably dimethylformamide, at about 80° C., for about 18 hours. When the reaction is substantially complete, the product of Formula I where $R^2$ is hydrogen is isolated by conventional means, for example by removal of the solvent under reduced pressure, partitioning between dichloromethane and water, separation of the organic layer, removal of solvent, followed by chromatography of the residue on silica gel.

Step 6—Preparation of Formula I where $R^2$ is Acyl

The compound of Formula I where $R^2$ is hydrogen is then converted to a compound of Formula I where $R^2$ is acyl, by reaction with a compound of formula RC(O)Cl, where RC(O)— represents $R^2$ when $R^2$ is defined as acyl, in the presence of a tertiary base, preferably triethylamine. The reaction is carried out in an inert solvent, preferably toluene, at about reflux temperature for about 18 hours. When the reaction is substantially complete, the product of Formula I where $R^2$ is acyl is isolated by conventional means, for example by partitioning the crude reaction mixture between dichloromethane and water, separating the organic layer, removing the solvent under reduced pressure, followed by chromatography of the residue on silica gel, preferably TLC.

Preparation of Formula (3) when $R^1$ is Aryl or Heteroaryl

A preferred method of preparing a compound of formula (3) in which $R^1$ is —Y-Z, in which Y is a covalent bond and Z is aryl or heteroaryl is to first react the dichloropurine of formula (1) with a optionally substituted aryl-trialkylstannane in the presence of a copper catalyst, for example copper acetate, and a source of fluoride ions, preferably tetrabutylammonium fluoride. This reaction is described in more detail in Tetrahedron Letters, 43 (2002), 3091–3094, the complete disclosure of which is hereby incorporated by reference.

The product is a 2,6-dichloro-7-arylpurine, which is then reacted as described in step 1 with an amine of formula $R_2NH_2$ to give a compound of formula (3) in which $R^1$ is optionally substituted aryl. This reaction is utilized to provide, for example, 2-chloro-6-amino-7-(3-carboxamido) phenyl, a compound of formula (3), which is then converted as shown in Reaction Scheme 1 to a compound of Formula I, for example $N^2$-[2-(3-fluorophenyl)ethylamino)-8-(pyrazol-1-yl)-9-(3-carboxamidophenyl)-9H-purine-2,6-diamine.

An alternative method for preparing compounds of Formula I is shown in Reaction Scheme 2, starting from a compound of formula (5).

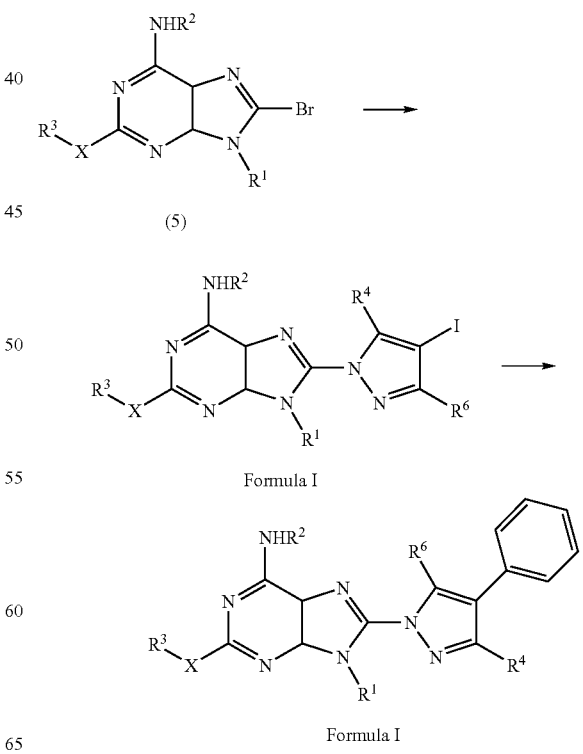

REACTION SCHEME 2

Step 1—Preparation of Formula I where $R^5$ is Iodo

The reaction is carried out as shown in Reaction Scheme 1 above, Step 5, reacting with an optionally substituted 4-iodopyrazole. The compound of Formula I where $R^5$ is iodo is isolated as before.

Step 2—Preparation of Formula I where $R^5$ is Optionally Substituted Phenyl

The compound of Formula I where $R^5$ is iodo is then converted to a compound of Formula I where $R^5$ is optionally substituted phenyl by reaction with an optionally substituted phenylboronic acid. The reaction is carried out in an inert solvent, preferably toluene, in the presence of aqueous sodium carbonate solution and tetrakis(triphenylphosphine) palladium(0), at about reflux temperature for about 24 hours. Excess boronic acid derivative is quenched by addition of hydrogen peroxide. When the reaction is substantially complete, the product of Formula I where $R^2$ is hydrogen is isolated by conventional means, for example by partitioning the crude reaction mixture between dichloromethane and water, separating the organic layer, removing the solvent under reduced pressure, followed by chromatography of the residue on silica gel, preferably TLC.

Formula I where $R^5$ is Ethyl

Similarly, the compound of Formula I where $R^5$ is iodo is converted to a compound of Formula I where $R^5$ is vinyl by reaction with tributylvinyltin, tetrakis(triphenylphosphine) palladium(0), and copper iodide. This compound is then hydrogenated in the presence of palladium on carbon catalyst to give a compound of Formula I where $R^5$ is ethyl.

Similarly, reacting the compound of Formula I where $R^5$ is iodo with tri(n-butyl)allyltin, a compound of Formula I where $R^5$ is allyl is produced, which may similarly be reduced to n-propyl.

An alternative method of introducing the pyrazole group to the 8-position of the purine is shown in Reaction Scheme 3.

REACTION SCHEME 3

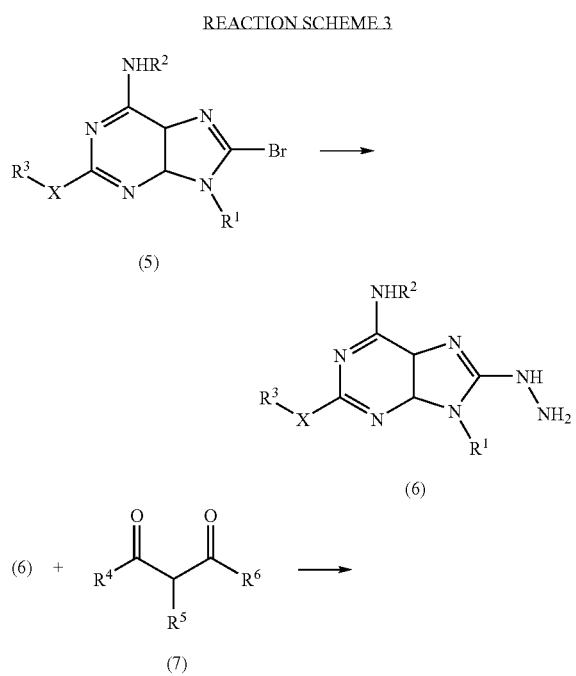

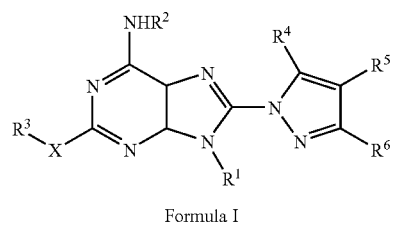

Formula I

Step 1—Preparation of Formula (6)

The compound of formula (5) is converted to a compound of formula (6) by reaction with hydrazine hydrate. The reaction is carried out in a protic solvent, preferably ethanol, at about reflux, preferably about 80° C., for about 24 hours. When the reaction is substantially complete, the product of formula (6) is isolated by conventional means, for example by partitioning between ether and water, separation of the organic layer, drying the solvent, and removal of solvent under reduced pressure. The compound of Formula (6) is used for the next step without purification.

Step 2—Preparation of Formula I

The compound of formula (6) is converted to a compound of Formula I by reaction with an optionally substituted 1,3-propanedione of formula (7). The reaction is carried out in a protic solvent, preferably methanol/acetic mixture, at about reflux, for about 24 hours. When the reaction is substantially complete, the product of Formula I is isolated by conventional means, for example by removal of solvent under reduced pressure, followed by chromatography of the residue on silica gel, preferably TLC.

Preferred Processes and Last Steps

The compounds of the present invention can be prepared according to the following last steps:

1. Contacting a compound of the formula

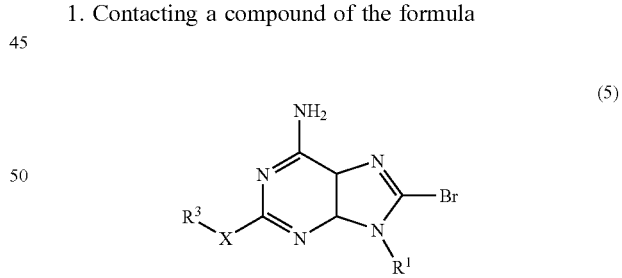

with an anion formed from a pyrazole of the formula:

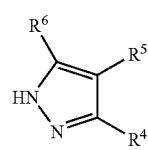

and a strong base, preferably sodium hydride.

2. Contacting a compound of Formula I in which $R^2$ is hydrogen:

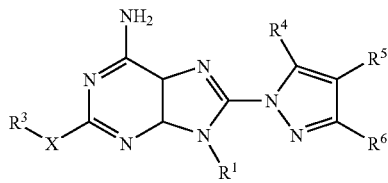

Formula I with an acid halide of the formula RC(O)Hal, where RC(O)— represents $R^2$ when $R^2$ is acyl, Hal is halogen, preferably chloro, in the presence of a base, preferably a tertiary amine.

3. Contacting a compound of formula (6):

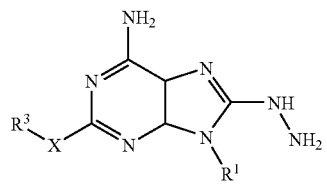

(6)

with an optionally substituted propanedione of the formula:

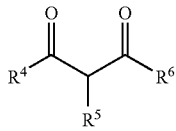

Utility, Testing and Administration

General Utility

The compounds of Formula I are effective in the treatment of conditions that respond to administration of $A_{2B}$ adenosine receptor antagonists. Such conditions include, but are not limited to, diarrhea, atherosclerosis, restenosis, diabetic retinopathy, cancer, senile dementia, Alzheimer's disease, Parkinson's disease, traumatic brain injury, and Type I hypersensitivity reactions, including asthma, atopic eczema, and hay fever.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

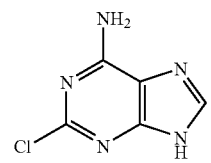

2

Preparation of a Compound of Formula
(2)-2-Chloropurine-6-ylamine

Ammonia was bubbled through 200 mL of methanol for 15 minutes, and the solution was added to 2,6-dichloropurine (10 g, 0.053 moles) in a steel bomb. The resulting mixture was then heated to 90° C. for 48 hours. Evaporation of the solvent followed by drying under vacuum afforded the compound of formula (2) (2-chloropurine-6-ylamine), as a yellow solid.

EXAMPLE 2

Preparation of a Compound of Formula (3)

A. Preparation of a Compound of Formula (3) where $R^1$ is Ethyl

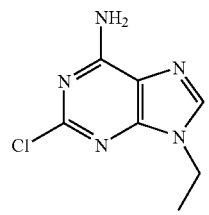

3

The compound of formula (2) (8.9 g, 0.053 mole), potassium carbonate (18.31 g, 0.133 mole), and ethyl iodide (6.36 mL, 0.08 moles) were combined in 100 mL of acetone and stirred at reflux for 18 hours. The mixture was cooled and the solvent evaporated. To the residue was added water (250 mL), and the mixture was filtered to give a compound of formula (3) where $R^1$ is ethyl (2-chloro-9-ethylpurine-6-ylamine), as a buff colored solid.

B. Preparation of a Compound of Formula (3) where $R^1$ is n-Propyl

Similarly, following the procedure of 1A above, but replacing ethyl iodide by n-propyl iodide, 2-chloro-9-(n-propyl)purine-6-ylamine was prepared.

C. Preparation of a Compound of Formula (3), Varying $R^1$

Similarly, following the procedure of 1A above, but replacing ethyl iodide by compounds with suitable leaving groups, the following compounds of formula (3) are prepared:

2-chloro-9-methylpurine-6-ylamine;
2-chloro-9-(iso-propyl)purine-6-ylamine;
2-chloro-9-(isobutyl)purine-6-yl amine;
2-chloro-9-(2-fluoropropyl)purine-6-ylamine;
2-chloro-9-(n-pentyl)purine-6-ylamine;
2-chloro-9-(n-decyl)purine-6-ylamine;
2-chloro-9-allylpurine-6-ylamine;
2-chloro-9-(hept-4-enyl)purine-6-ylamine;
2-chloro-9-(prop-2-ynyl)purine-6-ylamine;
2-chloro-9-cyclohexylmethylpurine-6-ylamine;
2-chloro-9-phenylethylpurine-6-ylamine;
2-chloro-9-(4-methoxy)phenylethylpurine-6-ylamine;
2-chloro-9-(4-pyridylprop-1-yl)purine-6-ylamine; and
2-chloro-9-(4-piperidinbut-1-yl)purine-6-ylamine.

D. Preparation of a Compound of Formula (3), Varying $R^1$

Similarly, following the procedure of 1A above, but replacing ethyl iodide by compounds with suitable leaving groups, any compound of formula (3) may be prepared.

EXAMPLE 3

Preparation of a Compound of Formula (4)

A. Preparation of a Compound of Formula (4) where $R^1$ is Ethyl, $R^3$ is Benzyl, and X is —NH—

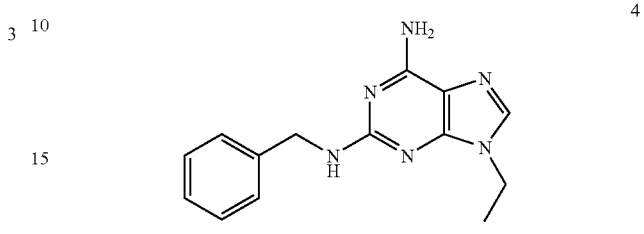

4

A compound of formula (3) where $R^1$ is ethyl (2-chloro-9-ethylpurine-6-ylamine) (0.9 g, 4.55 mmoles), triethylamine (1.27 mL, 9 mmoles), and benzylamine(1 mL, 9 mmoles) were mixed in 1-butanol (10 mL) and stirred at reflux for 24 hours. Another 1 mL of benzylamine was added and the refluxing continued for another 24 hours. Solvent was evaporated and the residue was purified over a silica gel column (eluting with 5% methanou/dichloromethane) to give a compound of formula (4) where $R^1$ is ethyl, $R^3$ is benzyl, and X is —NH— ($N^2$ benzyl-9-ethyl-9H-purine-2,6-diamine), as a pale yellow solid.

B. Preparation of a Compound of Formula (4) where $R^1$ is Ethyl, $R^3$ is 2-Phenylethyl, and X is —NH—

Similarly, following the procedure of 3A above, but replacing benzylamine with 2-phenyethylamine, ($N^2$(2-phenylethyl)-9-ethyl-9H-purine-2,6-diamine) was prepared, a compound of formula (4).

C. Preparation of a Compound of Formula (4), varying $R^1$ and $R^3$

Similarly, following the procedure of 3A above, but optionally replacing 2-chloro-9-ethylpurine-6-ylamine) with other compounds of formula (3), and optionally replacing benzylamine with other amines of formula $R^3NH_2$, the following compounds of formula (4) where X is NH are prepared.

$N^2$-benzyl-9-methylpurine-2,6-diamine;
$N^2$-benzyl-9-(iso-propyl)purine-6-diamine;
$N^2$ benzyl-9-isobutyl-9H-purine-2,6-diamine),
$N^2$ benzyl-9-(2-fluoropropyl)-9H-purine-2,6-diamine),
$N^2$ benzyl-9-(n-pentyl)-9H-purine-2,6-diamine),
$N^2$ benzyl-9-(n-pentyl)-9H-purine-2,6-diamine),
$N^2$ benzyl-9-(n-decyl)-9H-purine-2,6-diamine),
$N^2$ benzyl-9-allyl-9H-purine-2,6-diamine),
$N^2$ benzyl-9-(hept-4-enyl)-9H-purine-2,6-diamine),
$N^2$ benzyl-9-(n-prop-2ynyl)-9H-purine-2,6-diamine),
$N^2$ benzyl-9-(cyclohexylmethyl)-9H-purine-2,6-diamine),
$N^2$ benzyl-9-phenylethyl-9H-purine-2,6-diamine),
$N^2$ benzyl-9-(4-methoxyphenylethyl)-9H-purine-2,6-diamine),
$N^2$ benzyl-9-(4-pyridylprop-1-yl)-9H-purine-2,6-diamine),
$N^2$ benzyl-9-(4-piperidinbut-1-yl)-9H-purine-2,6-diamine),
$N^2$ benzyl-9-allyl-9H-purine-2,6-diamine),
$N^2$ benzyl-9-(hept-4-enyl)-9H-purine-2,6-diamine),
$N^2$ benzyl-9-(n-prop-2ynyl)-9H-purine-2,6-diamine), N² benzyl-9-(cyclohexylmethyl)-9H-purine-2,6-diamine),
N² ethyl-9-ethyl-9H-purine-2,6-diamine),
N² n-decyl-9-ethyl-9H-purine-2,6-diamine),
N² cyclopentyl-9-(n-propyl)-9H-purine-2,6-diamine),
N² cyclohexyl-9-(n-propyl)-9H-purine-2,6-diamine),
N² (2-hydroxycyclohexyl)-9-isopropyl-9H-purine-2,6-diamine),
N² phenyl-9-isopropyl-9H-purine-2,6-diamine),
N² (2-phenylethyl)-9-isopropyl-9H-purine-2,6-diamine),
N² (4-fluorobenzyl)-9-ispropyl-9H-purine-2,6-diamine),
N² (2-naphyth-1-ylethyl)-9-isobutyl-9H-purine-2,6-diamine),
N² pyrid-4-yl-9-isobutyl-9H-purine-2,6-diamine),
N² benzothiazol-2-yl-9-isobutyl-9H-purine-2,6-diamine),
N² pyrimidin-2-yl-9-isobutyl-9H-purine-2,6-diamine),
N² pyridin-3-ylmethyl-9-isobutyl-9H-purine-2,6-diamine),
N² (tetrahydrofuran-3-yl)-9-isobutyl-9H-purine-2,6-diamine),
N² (piperidin-4-ylmethyl)-9-isobutyl-9H-purine-2,6-diamine), and
N² (morpholin-3-yl)-9-isobutyl-9H-purine-2,6-diamine), D. Preparation of a Compound of Formula (4), Varying $R^1$, $R^3$, and X Similarly, following the procedure of 3A above, but optionally replacing 2-chloro-9-ethylpurine-6-ylamine) with other compounds of formula (3), and replacing benzylamine with a compound of formula $R^3XM$, where X is oxygen or sulfur and M is an alkali metal, and optionally replacing the solvent with a non-protic solvent, for example DMF, compounds of formula (4) where X is oxygen or sulfur are prepared.

EXAMPLE 4

Preparation of a Compound of Formula I

A. Preparation of a Compound of Formula I where $R^1$ is Ethyl, $R^2$ is Hydrogen, $R^3$ is Benzyl, $R^4$, $R^5$, $R^6$ are Hydrogen, and X is —NH—

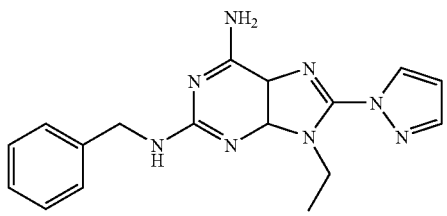

The compound of formula (4) where $R^1$ is ethyl, $R^3$ is benzyl, and X is —NH— (1 g, 3.72 mmoles) was dissolved in tetrahydrofuran (37.5 mL) and N-bromosuccinimide (0.73 g, 4.1 mmoles) added, and the mixture stirred at room temperature for 2 hours. The solvent was evaporated under reduced pressure, and the residue was purified on a silica gel column, eluting with 1:1 EtOAc:Hexanes to 2% methanol/dichloromethane, to give a compound of formula (5), N² benzyl-8-bromo-9-ethyl-9H-purine-2,6-diamine, as an off-white solid.

This compound (0.5 g, 1.68 mmoles) was dissolved in DMF (5 mL) and added to a previously formed mixture of pyrazole (0.34 g, 5 mmoles) and 60% w/w NaH dispersion in DMF (10 mL). The reaction mixture was allowed to stir at 80° C. for 18 hours. The solvent was evaporated under reduced pressure, and the crude material was dissolved in 50 mL dichloromethane and washed with water (2×20 mL). The dichloromethane was dried (MgSO₄) and removed under reduced pressure, to give a residue that was purified by column chromatography (eluting with 30% EtOAc/hexanes to 75% EtOAc/hexanes) to give N² benzyl-8-(pyrazol-1-yl)-9-ethyl-9H-purine-2,6-diamine, as a pale yellow solid, which is a compound of Formula I where $R^1$ is ethyl, $R^3$ is benzyl, $R^4$, $R^5$, $R^6$ are hydrogen, and X is —NH—.

B. Preparation of a Compound of Formula I where $R^1$ is Ethyl, $R^2$ is Hydrogen, $R^3$ is 2-Phenylethyl, and X is —NH—

Similarly, following the procedure of 4A above, but replacing the compound of formula (4) where $R^1$ is ethyl, $R^3$ is benzyl, and X is —NH— with a compound of formula (4) where $R^1$ is ethyl, $R^3$ is 2-phenylethyl, and X is —NH—, the compound of Formula I where $R^1$ is ethyl, $R^3$ is 2-phenylethyl, and X is —NH—, (N²(2-phenylethyl)-8-(pyrazol-1-yl)-9-ethyl-9H-purine-2,6-diamine) was prepared.

Similarly, the following compounds of Formula I were prepared:

N² benzyl-9-ethyl-8-(4-iodopyrazol-1-yl)-9H-purine-2,6-diamine;

N² benzyl-9-ethyl-8-(4-methylpyrazol-1-yl)-9H-purine-2,6-diamine;

N² benzyl-9-ethyl-8-[3-(4-methylphenyl)pyrazol-1-yl]-9H-purine -2,6-diamine;

N² (2-phenylethyl)-9-ethyl-8-(pyrazol-1-yl)-9H-purine-2,6-diamine;

N² (1R-1-phenylethyl)-9-ethyl -8-(4-methyl pyrazol-1-yl)-9H-purine-2,6-diamine;

N² (3-phenylpropyl)-9-propyl-8-(pyrazol-1-yl)-9H-purine-2,6-diamine;

N² [2-(2-fluorophenyl)ethyl]-9-9-propyl-8-(pyrazol-1-yl)-9H-purine-2,6-diamine.

N² phenylethyl-8-(pyrazol-1-yl)-9-(3,3,3-trifluoropropyl)-9H-purine-2,6-diamine;

N² (2-phenylpropyl)-9-propyl-8-(pyrazol-1-yl)-9H-purine-2,6-diamine, R and S isomers;

N² [2-(4-chlorophenyl)ethyl)-9-propyl-8-(pyrazol-1-yl)-9H-purine-2,6-diamine;

N² [2-(2-chlorophenyl)ethyl)-9-propyl-8-(pyrazol-1-yl)-9H-purine-2,6-diamine;

N² [1-phenyl)ethyl)-9-propyl-8-(4-methylpyrazol-1-yl)-9H-purine-2,6-diamine;

N² [2-(2,5-dimethoxyphenyl)ethyl)-9-propyl-8-(pyrazol-1-yl)-9H-purine-2,6-diamine;

N² [2-(2,4-dichlorophenyl)ethyl)-9-propyl-8-(pyrazol-1-yl)-9H-purine-2,6-diamine;

N² [2-(2-methoxyphenyl)ethyl)-9-propyl-8-(pyrazol-1-yl)-9H-purine-2,6-diamine;

N² 2-phenylethyl-N⁶-isobutyl-9-propyl-8-(pyrazol-1-yl)-9H-purine-2,6-diamine;

N² (2-hydroxymethyl)benzyl-9-propyl-8-(pyrazol-1-yl)-9H-purine-2,6-diamine;

N² (4-aminomethylbenzyl)-9-propyl-8-(pyrazol-1-yl)-9H-purine-2,6-diamine;

N² (3-aminomethylbenzyl)-9-propyl-8-(pyrazol-1-yl)-9H-purine-2,6-diamine;

N² (2-aminomethylbenzyl)-9-propyl-8-(pyrazol-1-yl)-9H-purine-2,6-diamine;

N² (4-hydroxymethyl)benzyl-9-propyl-8-(pyrazol-1-yl)-9H-purine-2,6-diamine;

$N^2$ (3-hydroxymethyl)benzyl-9-propyl-8-(pyrazol-1-yl)-9H-purine-2,6-diamine;

$N^2$ [2-(4-fluorophenyl)ethyl]-9-propyl-8-(pyrazol-1-yl)-9H-purine-2,6-diamine; and $N^2$ [2-(3-fluorophenyl)ethyl]-9-propyl-8-(pyrazol-1-yl)-9H-purine-2,6-diamine;

C. Preparation of a Compound of Formula I, Varying $R^1$, $R^2$, $R^3$, $R^4$, $R^5$, $R^6$, and X Similarly, following the procedure of 4A above, but replacing the compound of formula (4) where $R^1$ is ethyl, $R^3$ is benzyl, and X is —NH— with other appropriately substituted compounds of formula (4), the following compounds of Formula I are prepared.

$N^2$ benzyl-8-(pyrazol-1-yl)-9-methyl-9H-purine-2,6-diamine;

$N^2$ benzyl-8-(pyrazol-1-yl)-9-isopropyl-9H-purine-2,6-diamine;

$N^2$ benzyl-8-(4-trifluoromethylpyrazol-1-yl)-9-ethyl-9H-purine-2,6-diamine, $N^2$ benzyl-8-(3-methylpyrazol-1-yl)-9-ethyl-9H-purine-2,6-diamine, $N^2$ benzyl-8-(3-phenyl-4-fluoropyrazol-1-yl)-9-ethyl-9H-purine-2,6-diamine, $N^2$ benzyl-8-[3-(pyrid-1-yl)pyrazol-1-yl]-9-ethyl-9H-purine-2,6-diamine, $N^2$ benzyl-8-(pyrazol-1-yl)-9-isobutyl-9H-purine-2,6-diamine), $N^2$ benzyl-8-(pyrazol-1-yl)-9-(2-fluoropropyl)-9H-purine-2,6-diamine), $N^2$ benzyl-8-(pyrazol-1-yl)-9-(n-pentyl)-9H-purine-2,6-diamine), $N^2$ benzyl-8-(pyrazol-1-yl)-9-(n-decyl)-9H-purine-2,6-diamine), $N^2$ benzyl-8-(pyrazol-1-yl)-9-allyl-9H-purine-2,6-diamine), $N^2$ benzyl-8-(pyrazol-1-yl)-9-(hept-4-enyl)-9H-purine-2,6-diamine), $N^2$ benzyl-8-(pyrazol-1-yl)-9-(n-prop-2ynyl)-9H-purine-2,6-diamine), $N^2$ benzyl-8-(pyrazol-1-yl)-9-(cyclohexylmethyl)-9H-purine-2,6-diamine), $N^2$ benzyl-8-(pyrazol-1-yl)-9-phenylethyl-9H-purine-2,6-diamine), $N^2$ benzyl-8-(pyrazol-1-yl)-9-(4-methoxyphenylethyl)-9H-purine-2,6-diamine), $N^2$ benzyl-8-(pyrazol-1-yl)-9-(4-pyridylprop-1-yl)-9H-purine-2,6-diamine), $N^2$ benzyl-8-(pyrazol-1-yl)-9-(4-piperidinbut-1-yl)-9H-purine-2,6-diamine), $N^2$ benzyl-8-(pyrazol-1-yl)-9-allyl-9H-purine-2,6-diamine), $N^2$ benzyl-8-(pyrazol-1-yl)-9-(hept-4-enyl)-9H-purine-2,6-diamine), $N^2$ benzyl-8-(pyrazol-1-yl)-9-(n-prop-2ynyl)-9H-purine-2,6-diamine), $N^2$ benzyl-8-(pyrazol-1-yl)-9-(cyclohexylmethyl)-9H-purine-2,6-diamine), $N^2$ ethyl-8-(pyrazol-1-yl)-9-ethyl-9H-purine-2,6-diamine), $N^2$ n-decyl-8-(pyrazol-1-yl)-9-ethyl-9H-purine-2,6-diamine), $N^2$ cyclopentyl-8-(pyrazol-1-yl)-9-(n-propyl)-9H-purine-2,6-diamine), $N^2$ cyclohexyl-8-8pyrazol-1-yl)-9-(n-propyl)-9H-purine-2,6-diamine), $N^2$ (2-hydroxycyclohexyl)-8-pyrazol-1-yl)-9-isopropyl-9H-purine-2,6-diamine), $N^2$ phenyl-8-(pyrazol-1-yl)-9-isopropyl-9H-purine-2,6-diamine), $N^2$ (2-phenylethyl)-8-(pyrazol-1-yl)-9-isopropyl-9H-purine-2,6-diamine), $N^2$ (4-fluorobenzyl)-8-(pyrazol-1-yl)-9-isopropyl-9H-purine-2,6-diamine), $N^2$ (2-naphyth-1-ylethyl)-8-(pyrazol-1-yl)-9-isobutyl-9H-purine-2,6-diamine), $N^2$ pyrid-4-yl-8-(pyrazol-1-yl)-9-isobutyl-9H-purine-2,6-diamine), $N^2$ benzothiazol-2-yl-8-(pyrazol-1-yl)-9-isobutyl-9H-purine-2,6-diamine), $N^2$ pyrimidin-2-yl-8-(pyrazol-1-yl)-9-isobutyl-9H-purine-2,6-diamine), $N^2$ pyridin-3-ylmethyl-8-(pyrazol-1-yl)-9-isobutyl-9H-purine-2,6-diamine), $N^2$ (tetrahydrofuran-3-yl)-8-(pyrazol-1-yl)-9-isobutyl-9H-purine-2,6-diamine), $N^2$ (piperidin-4-ylmethyl)-8-(pyrazol-1-yl)-9-isobutyl-9H-purine-2,6-diamine), and $N^2$ (morpholin-3-yl)-8-(pyrazol-1-yl)-9-isobutyl-9H-purine-2,6-diamine), D. Preparation of a Compound of Formula I, Varying $R^1$, $R^2$, $R^3$, $R^4$, $R^5$, $R^6$, and X Similarly, following the procedure of 4A above, but replacing the compound of formula (4) where $R^1$ is ethyl, $R^3$ is benzyl, and X is —NH— with other appropriately substituted compounds of formula (4), other compounds of Formula I are prepared.

EXAMPLE 5

Alternative Preparation of a Compound of Formula I

A. Preparation of a Compound of Formula I where $R^1$ is Ethyl, $R^2$ is Hydrogen, $R^3$ is Benzyl, $R^4$ and $R^6$ are Hydrogen, $R^5$ is Phenyl, and X is —NH—

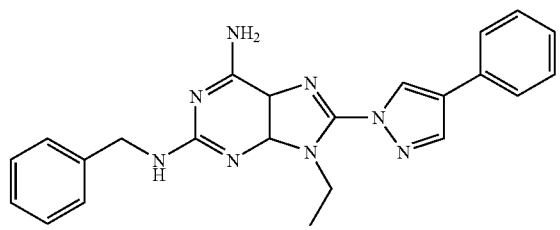

To a compound of formula (5), $N^2$ benzyl-8-(4-iodopyrazol-1-yl)-9-ethyl-9H-purine-2,6-diamine (50 mg, 0.1 mmoles), in toluene, was added p-tolyl boronic acid (30 mg, 0.2 mmoles, pre-dissolved in 0.2 mL of ethanol), followed by 0.2 mL of 2M aqueous sodium carbonate solution. Nitrogen was bubbled through before and after adding Pd(PPh3)4 (4 mg) and the reaction mixture was stirred at reflux for 24 hours. The excess boronic acid was quenched by the addition of 30% hydrogen peroxide, and dichloromethane added. The organic phase was separated, concentrated, and the residue obtained was purified by preparative TLC (eluting with 1:1 EtOAc:Hexanes) to give a compound of Formula I where $R^1$ is ethyl, $R^3$ is benzyl, $R^4$ and $R^6$ are hydrogen, $R^5$ is phenyl, and X is —NH— ($N^2$ benzyl-8-[4-(4-methylphenyl)pyrazol-1-yl]-9-ethyl-9H-purine-2,6-diamine) as a white solid.

B. Preparation of a Compound of Formula I where $R^1$ is Ethyl, $R^2$ is Hydrogen, $R^3$ is Benzyl, $R^4$ and $R^6$ are Hydrogen, $R^5$ is 4-FluoroPhenyl, and X is —NH—

Similarly, following the procedure of 5A above, but substituting 4-fluorophenyl boronic acid for phenyl boronic acid, the compound of Formula I where $R^1$ is ethyl, $R^3$ is benzyl, $R^4$ and $R^6$ are hydrogen, $R^5$ is 4-fluorophenyl, and X is —NH—, ($N^2$ benzyl-8-[4-(4-fluorophenyl)pyrazol-1-yl]-9-ethyl-9H-purine-2,6-diamine) was prepared.

Similarly, the following compounds of formula I were prepared:
  $N^2$ benzyl-8-[4-(4-methoxyphenyl)pyrazol-1-yl]-9-ethyl-9H-purine-2,6-diamine; and
  $N^2$ benzyl-8-[4-(3-trifluoromethylphenyl)pyrazol-1-yl]-9-ethyl-9H-purine-2,6-diamine.

C. Preparation of a Compound of Formula I, Varying $R^1$, $R^2$, $R^3$, $R^4$, $R^5$, $R^6$, and X Similarly, following the procedure of 5A above, but optionally replacing $N^2$ benzyl-8-(4-iodopyrazol-1-yl)-9-ethyl-9H-purine-2,6-diamine with other appropriately substituted compounds of Formula I where $R^5$ is iodo, and optionally replacing phenyl boronic acid with other appropriately substituted phenyl boronic acids, other compounds of Formula I are prepared.

EXAMPLE 6

Preparation of a Compound of Formula I

A. Preparation of a Compound of Formula I where $R^1$ is Ethyl, $R^2$ is Hydrogen, $R^3$ is Benzyl, $R^4$ and $R^6$ are Hydrogen, $R^5$ is Vinyl, and X is —NH—

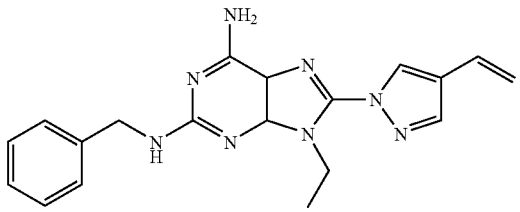

To a compound of Formula I where $R^5$ is iodo, $N^2$ benzyl-8-(4-iodopyrazol-1-yl)-9-ethyl-9H-purine-2,6-diamine (50 mg, 0.1 mmoles) in DMF (0.5 mL), was added tributylvinyl tin (70 mg, 0.2 mmoles), tetrakis(triphenylphosphine)palladium(0), and CuI (60 mg). Nitrogen was bubbled through the reaction mixture for one minute, and it was then heated at 100° C. for 24 hours with vigorous stirring. The solvent was removed under reduced pressure, and the residue was purified by preparative TLC (eluting with 1:1 EtOAc:Hexanes) to give a compound of Formula I where $R^1$ is ethyl, $R^3$ is benzyl, $R^4$ and $R^6$ are hydrogen, $R^5$ is vinyl, and X is —NH— ($N^2$ benzyl-8-(4-vinylpyrazol-1-yl)-9-ethyl-9H-purine-2,6-diamine), as a yellow solid.

B. Preparation of a Compound of Formula I where $R^1$ is Ethyl, $R^2$ is Hydrogen, $R^3$ is Benzyl, $R^4$ and $R^6$ are Hydrogen, $R^5$ is Allyl, and X is —NH—

Similarly, following the procedure of 6A above, but substituting tri(n-butyl)allyltin for tributylvinyltin, the compound of Formula I where $R^1$ is ethyl, $R^3$ is benzyl, $R^4$ and $R^6$ are hydrogen, $R^5$ is allyl, and X is —NH—, ($N^2$ benzyl-8-[4-allylpyrazol-1-yl]-9-ethyl-9H-purine-2,6-diamine) was prepared.

C. Preparation of a Compound of Formula I, Varying $R^1$, $R^2$, $R^3$, $R^4$, $R^5$, $R^6$, and X Similarly, following the procedure of 6A above, but optionally replacing $N^2$ benzyl-8-(4-iodopyrazol-1-yl)-9-ethyl-9H-purine-2,6-diamine with other appropriately substituted compounds of Formula I where $R^5$ is iodo, and optionally replacing tributylvinyl tin with other appropriately substituted tin compounds, other compounds of Formula I are prepared.

EXAMPLE 7

Preparation of a Compound of Formula I

A. Preparation of a Compound of Formula I where $R^1$ is Ethyl, $R^2$ is Hydrogen, $R^3$ is Benzyl, $R^4$ and $R^6$ are Hydrogen, $R^5$ is Ethyl, and X is —NH—

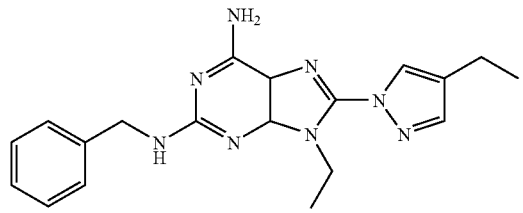

$N^2$ benzyl-8-[3-(4-vinylphenyl)pyrazol-1-yl]-9-ethyl-9H-purine-2,6-diamine, a compound of Formula I (25 mg, 0.05 mmoles), was dissolved in methanol (2 mL), and to this solution was added 20% w/w Pd/C. The reaction mixture was stirred at room temperature under hydrogen at 1 atmosphere. After 2 hours, the reaction mixture was filtered over celite, solvent evaporated under reduced pressure, and the residue obtained was purified by preparative TLC (eluting with 1:1 EtOAc:Hexanes) to give $N^2$ benzyl-8-[3-(4-ethylphenyl)pyrazol-1-yl]-9-ethyl-9H-purine-2,6-diamine as a yellow solid. Similarly, reduction of $N^2$ benzyl-8-[4-allylpyrazol-1-yl]-9-ethyl-9H-purine-2,6-diamine affords $N^2$ benzyl-8-[4-propylpyrazol-1-yl]-9-ethyl-9H-purine-2,6-diamine.

EXAMPLE 8

Alternative Preparation of a Compound of Formula I

A. Preparation of a Compound of Formula (6) where $R^1$ is Ethyl, $R^2$ is Hydrogen, $R^3$ is Benzyl, and X is —NH—

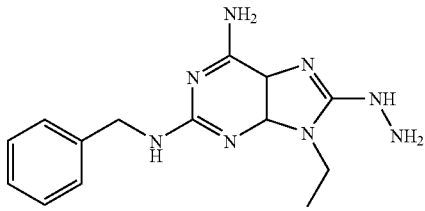

The compound of formula (5) where $R^1$ is ethyl, $R^3$ is benzyl, and X is —NH— (1.0 g, 2.9 mmoles) and hydrazine monohydrate (0.5 mL, 10.3 mmoles) were dissolved in ethanol (5 mL) and the mixture warmed to reflux for 24 hours. The precipitate obtained was stirred in ether for 30 minutes. The precipitate was filtered and dried to give a compound of formula (6) where $R^1$ is ethyl, $R^3$ is benzyl, and X is —NH—, which was used in the next step without further purification.

B. Preparation of a Compound of Formula I where $R^1$ is Ethyl, $R^2$ is Hydrogen, $R^3$ is Benzyl, $R^4$ and $R^6$ are Methyl, $R^5$ is Hydrogen, and X is —NH—

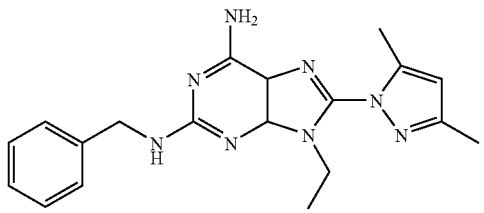

The crude compound of formula (6) where $R^1$ is ethyl, $R^3$ is benzyl, and X is —NH— (0.1 g, 0.33 mmoles) was dissolved in 1:1 MeOH:AcOH solution (4 mL). To this solution was added 2,4-pentanedione (0.5 mmoles), a compound of formula (7) in which $R^4$, $R^5$, and $R^6$ are all hydrogen, and the mixture was refluxed for 24 hours. The solvents were evaporated under reduced pressure, and the residue was purified by preparative TLC (eluting with EtOAc) to give a compound of Formula I where $R^1$ is ethyl, $R^3$ is benzyl, $R^4$ and $R^6$ are methyl, $R^5$ is hydrogen, and X is —NH—, as an orange solid.

C. Preparation of a Compound of Formula I, Varying $R^1$, $R^2$, $R^3$, $R^4$, $R^5$, $R^6$, and X Similarly, following the procedure of 8A above, but optionally replacing the compound of formula (5) where $R^1$ is ethyl, $R^3$ is benzyl, and X is —NH— with other compounds of formula (5) in 8A above, and optionally replacing 2,4-pentanedione with other appropriately substituted compounds of formula (7), other compounds of Formula I are prepared.

EXAMPLE 9

Preparation of a Compound of Formula I

A. Preparation of a Compound of Formula I where $R^1$ is Ethyl, $R^2$ is 2,2-Dimethylpropionyl, $R^3$ is Benzyl, $R^4$, $R^5$, $R^6$ are Hydrogen, and X is —NH—

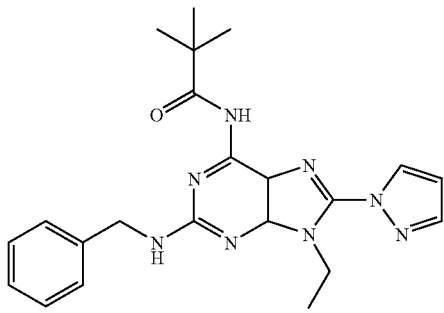

To a solution of a compound of Formula I where $R^1$ is ethyl, $R^2$ is hydrogen, $R^3$ is benzyl, $R^4$, $R^5$, $R^6$ are hydrogen, and X is —NH— (10 mg, 0.03 mmoles) in toluene (0.5 mL) was added pivaloyl chloride (7 μL, 0.06 mmoles), triethylamine (20 μL, 0.15 mmoles) and the mixture was refluxed for 18 hours. The reaction mixture was diluted with dichloromethane, washed with saturated NaHCO3 (3 mL) and dried over MgSO4. Evaporation of solvent gave a residue which was purified by preparative TLC (eluting with 35% EtOAc/Hexanes) to afford a compound of Formula I where $R^1$ is ethyl, $R^2$ is 2,2-dimethylpropionyl, $R^3$ is benzyl, $R^4$, $R^5$, $R^6$ are hydrogen, and X is —NH— ($N^2$ benzyl-$N^6$-(2,2-dimethylpropionyl) 8-(pyrazol-1-yl)-9-ethyl-9H-purine-2,6-diamine), as an off-white solid.

B. Preparation of a Compound of Formula I where $R^1$ is Ethyl, $R^3$ is Benzyl, $R^4$, $R^5$, $R^6$ are Hydrogen, and X is —NH—, Varying $R^2$ Similarly, following the procedure of 9A above, but optionally replacing the compound of Formula I in which $R^1$ is ethyl, $R^2$ is hydrogen, $R^3$ is benzyl, $R^4$, $R^5$, $R^6$ are hydrogen, and X is —NH— with other appropriately substituted compounds of Formula I, and optionally substituting 3-chlorocarbonyl-propionic acid ethyl ester for other compounds of formula RC(O)Cl, where RC(O)— represents $R^2$ when $R^2$ is acyl, the following compounds of Formula I were made:

$N^2$ benzyl-$N^6$-(3-ethoxycarbonylpropionyl) 8-(pyrazol-1-yl)-9-ethyl-9H-purine-2,6-diamine);
$N^2$ benzyl-$N^6$-(2-methoxyacetyl) 8-(pyrazol-1-yl)-9-ethyl-9H-purine-2,6-diamine);
$N^2$ benzyl-$N^6$-(2,2-dimethylpropionyl) 8-[(4-methylphenyl)-4-pyrazol-1-yl]-9-ethyl-9H-purine-2,6-diamine);
$N^2$ benzyl-$N^6$-(2,2-dimethylpropionyl) 8-[(4-methylphenyl)-4-pyrazol-1-yl]-9-propyl-9H-purine-2,6-diamine);
$N^2$ phenylethyl-$N^6$-(benzoyl)-8-(pyrazol-1-yl)-9-(prop-1-yl)-9H-purine-2,6-diamine);
$N^2$ benzyl-$N^6$-(2,2-dimethylpropionyl) 8-(4-methylpyrazol-1-yl-9-ethyl-9H-purine-2,6-diamine);
$N^2$ phenylethyl-$N^6$-(4-t-butylbenzoyl)-8-(pyrazol-1-yl)-9-(prop-1-yl)-9H-purine-2,6-diamine);
$N^2$ phenylethyll-$N^6$-(3,4-difluorobenzoyl)-8-(pyrazol-1-yl)-9-(prop-1-yl)-9H-purine-2,6-diamine);
$N^2$ phenylethyl-$N^6$-(3-trifluoromethylbenzoyl)-8-(pyrazol-1-yl)-9-(prop-1-yl)-9H-purine-2,6-diamine);
$N^2$ phenylethyl-$N^6$-(3,5-dimethoxybenzoyl)-8-(pyrazol-1-yl)-9-(prop-1-yl)-9H-purine-2,6-diamine);
$N^2$ phenylethyl-$N^6$-(4-cyanobenzoyl)-8-(pyrazol-1-yl)-9-(prop-1-yl)-9H-purine-2,6-diamine);
$N^2$ phenylethyl-$N^6$-(4-phenylbenzoyl)-8-(pyrazol-1-yl)-9-(prop-1-yl)-9H-purine-2,6-diamine);
$N^2$ phenylethyl-$N^6$-(3,4-methylenedioxybenzoyl)-8-(pyrazol-1-yl)-9-(prop-1-yl)-9H-purine-2,6-diamine);
$N^2$ phenylethyl-$N^6$-(2-methylpropanoyl)-8-(pyrazol-1-yl)-9-(prop-1-yl)-9H-purine-2,6-diamine);
$N^2$ phenylethyl-$N^6$-(cyclopropanoyl)-8-(pyrazol-1-yl)-9-(prop-1-yl)-9H-purine-2,6-diamine);
$N^2$ phenylethyl-$N^6$-(cyclobutanoyl)-8-(pyrazol-1-yl)-9-(prop-1-yl)-9H-purine-2,6-diamine);
$N^2$ phenylethyl-$N^6$-(cyclopentanoyl)-8-(pyrazol-1-yl)-9-(prop-1-yl)-9H-purine-2,6-diamine);
$N^2$ phenylethyl-$N^6$-(cyclohexanoyl)-8-(pyrazol-1-yl)-9-(prop-1-yl)-9H-purine-2,6-diamine);
$N^2$ phenylethyl-$N^6$-(2-methylbutanoyl)-8-(pyrazol-1-yl)-9-(prop-1-yl)-9H-purine-2,6-diamine);
$N^2$ phenylethyl-$N^6$-(2-ethylbutanoyl)-8-(pyrazol-1-yl)-9-(prop-1-yl)-9H-purine-2,6-diamine);
$N^2$ phenylethyl-$N^6$-(2,2,-diimethylpropanoyl)-8-(pyrazol-1-yl)-9-(prop-1-yl)-9H-purine-2,6-diamine);
$N^2$ phenylethyl-$N^6$-(2,2,-diimethylpropanoyl)-8-(4-methylpyrazol-1-yl)-9-(prop-1-yl)-9H-purine-2,6-diamine);
$N^2$ phenylethyl-$N^6$-(2,2-diphenylacetyl)-8-(pyrazol-1-yl)-9-(prop-1-yl)-9H-purine-2,6-diamine);
$N^2$ phenylethyl-$N^6$-(bicyclo[2.2.1]hept-5-an 2-carbonyl)-8-(pyrazol-1-yl)-9-(prop-1-yl)-9H-purine-2,6-diamine);

N² phenylethyl-N⁶-(2,3-dihydroxybicyclo[2.2.1]hept-5-en 2-carbonyl)-8-(pyrazol-1-yl)-9-(prop-1-yl)-9H-purine-2,6-diamine);

N² phenylethyl-N⁶-(2-n-propylpentanoyl)-8-(pyrazol-1-yl)-9-(prop-1-yl)-9H-purine-2,6-diamine); and N² phenylethyl-N⁶-(2-methylpentanoyl)-8-(pyrazol-1-yl)-9-(prop-1-yl)-9H-purine-2,6-diamine).

C. Preparation of a Compound of Formula I, Varying R¹, R², R³, R⁴, R⁵, R⁶, and X Similarly, following the procedure of 9A above, but optionally replacing the compound of Formula I in which the compound of Formula I where R¹ is ethyl, R² is hydrogen, R³ is benzyl, R⁴, R⁵, R⁶ are hydrogen, and X is —NH— with other appropriately substituted compounds of Formula I, and optionally substituting 3-chlorocarbonyl-propionic acid ethyl ester for other compounds of formula RC(O)Cl, the following compounds of Formula I are made.

N² benzyl-N⁶-(2,2-dimethylpropionyl) 8-(4-trifluoromethylpyrazol-1-yl)-9-ethyl-9H-purine-2,6-diamine, N² benzyl-N⁶-(2,2-dimethylpropionyl) 8-(3-methylpyrazol-1-yl)-9-ethyl-9H-purine-2,6-diamine, N² benzyl-N⁶-(2,2-dimethylpropionyl) 8-(3-phenyl-4-fluoropyrazol-1-yl)-9-ethyl-9H-purine-2,6-diamine, N² benzyl-N⁶-(2,2-dimethylpropionyl) 8-[3-(pyrid-1-yl) pyrazol-1-yl)-9-ethyl-9H-purine-2,6-diamine, N² benzyl-N⁶-(2,2-dimethylpropionyl) 8-(pyrazol-1-yl)-9-isobutyl-9H-purine-2,6-diamine), N² benzyl-N⁶-(2,2-dimethylpropionyl) 8-(pyrazol-1-yl)-9-(2-fluoropropyl)-9H-purine-2,6-diamine), N² benzyl-N⁶-(2,2-dimethylpropionyl) 8-(pyrazol-1-yl)-9-(n-pentyl)-9H-purine-2,6-diamine), N² benzyl-N⁶-(2,2-dimethylpropionyl) 8-(pyrazol-1-yl)-9-(n-decyl)-9H-purine-2,6-diamine), N² benzyl-N⁶-(2,2-dimethylpropionyl) 8-(pyrazol-1-yl)-9-allyl-9H-purine-2,6-diamine), N² benzyl-N⁶-(2,2-dimethylpropionyl) 8-(pyrazol-1-yl)-9-(hept-4-enyl)-9H-purine-2,6-diamine), N² benzyl-N⁶-(2,2-dimethylpropionyl) 8-(pyrazol-1-yl)-9-(n-prop-2ynyl)-9H-purine-2,6-diamine), N² benzyl-N⁶-(2,2-dimethylpropionyl) 8-(pyrazol-1-yl)-9-(cyclohexylmethyl)-9H-purine-2,6-diamine), N² benzyl-N⁶-(2,2-dimethylpropionyl) 8-(pyrazol-1-yl)-9-phenylethyl-9H-purine-2,6-diamine), N² benzyl-N⁶-(2,2-dimethylpropionyl) 8-(pyrazol-1-yl)-9-(4-methoxyphenylethyl)-9H-purine-2,6-diamine), N² benzyl-N⁶-(2,2-dimethylpropionyl) 8-(pyrazol-1-yl)-9-(4-pyridylprop-1-yl)-9H-purine-2,6-diamine), N² benzyl-N6-(2,2-dimethylpropionyl) 8-(pyrazol-1-yl)-9-(4-piperidinbut-1-yl)-9H-purine-2,6-diamine), N² benzyl-N⁶-(2,2-dimethylpropionyl) 8-(pyrazol-1-yl)-9-allyl-9H-purine-2,6-diamine), N² benzyl-N⁶-(2,2-dimethylpropionyl) 8-(pyrazol-1-yl)-9-(hept-4-enyl)-9H-purine-2,6-diamine), N² benzyl-N⁶-(2,2-dimethylpropionyl) 8-(pyrazol-1-yl)-9-(n-prop-2ynyl)-9H-purine-2,6-diamine), N² benzyl-N⁶-(2,2-dimethylpropionyl) 8-(pyrazol-1-yl)-9-(cyclohexylmethyl)-9H-purine-2,6-diamine), N² ethyl-N⁶-(2,2-dimethylpropionyl) 8-(pyrazol-1-yl)-9-ethyl-9H-purine-2,6-diamine), N² n-decyl-N⁶-(2,2-dimethylpropionyl) 8-(pyrazol-1-yl)-9-ethyl-9H-purine-2,6-diamine), N² cyclopentyl-N⁶-(2,2-dimethylpropionyl) 8-(pyrazol-1-yl)-9-(n-propyl)-9H-purine-2,6-diamine), N² cyclohexyl-N⁶-(2,2-dimethylpropionyl) 8-(pyrazol-1-yl)-9-(n-propyl)-9H-purine-2,6-diamine), N² (2-hydroxycyclohexyl)-N⁶-(2,2-dimethylpropionyl) 8-(pyrazol-1-yl)-9-isopropyl-9H-purine-2,6-diamine), N² phenyl-N⁶-(2,2-dimethylpropionyl) 8-(pyrazol-1-yl)-9-isopropyl-9H-purine-2,6-diamine), N² (2-phenylethyl)-N⁶-(2,2-dimethylpropionyl) 8-(pyrazol-1-yl)-9-isopropyl-9H-purine-2,6-diamine), N² (4-fluorobenzyl)-N⁶-(2,2-dimethylpropionyl)8-(pyrazol-1-yl)-9-isopropyl-9H-purine-2,6-diamine), N² (2-naphyth-1-ylethyl)-N⁶-(2,2-dimethylpropionyl) 8-(pyrazol-1-yl)-9-isobutyl-9H-purine-2,6-diamine), N² pyrid-4-yl-N⁶-(2,2-dimethylpropionyl) 8-(pyrazol-1-yl)-9-isobutyl-9H-purine-2,6-diamine), N² benzothiazol-2-yl-N⁶-(2,2-dimethylpropionyl) 8-(pyrazol-1-yl)-9-isobutyl-9H-purine-2,6-diamine), N² pyrimidin-2-yl-N⁶-(2,2-dimethylpropionyl) 8-(pyrazol-1-yl)-9-isobutyl-9H-purine-2,6-diamine), N² pyridin-3-ylmethyl-N⁶-(2,2-dimethylpropionyl) 8-(pyrazol-1-yl)-9-isobutyl-9H-purine-2,6-diamine), N² (tetrahydrofuran-3-yl)-N⁶-(2,2-dimethylpropionyl) 8-(pyrazol-1-yl)-9-isobutyl-9H-purine-2,6-diamine), N² (piperidin-4-ylmethyl)-N⁶-(2,2-dimethylpropionyl) 8-(pyrazol-1-yl)-9-isobutyl-9H-purine-2,6-diamine), and N² (morpholin-3-yl)-N⁶-(2,2-dimethylpropionyl) 8-(pyrazol-1-yl)-9-isobutyl-9H-purine-2,6-diamine), D. Preparation of a Compound of Formula I, Varying R¹, R², R³, R⁴, R⁵, R⁶, and X Similarly, following the procedure of 9A above, but optionally replacing the compound of Formula I in which the compound of Formula I where R¹ is ethyl, R² is hydrogen, R³ is benzyl, R⁴, R⁵, R⁶ are hydrogen, and X is —NH— with other appropriately substituted compounds of Formula I, and optionally substituting 3-chlorocarbonyl-propionic acid ethyl ester for other compounds of formula RC(O)Cl, the other compounds of Formula I are made.

The following examples illustrate the preparation of representative pharmaceutical formulations containing a compound of Formula I, such as those prepared in accordance with Example 1.

EXAMPLE 10

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 11

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 12

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 13

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 14

Suppositories, each containing 25 mg of active ingredient are made as follows:

| Ingredient | Amount |
|---|---|
| Actiye Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 15

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 16

A subcutaneous formulation may be prepared as follows:

| Ingredient | Quantity |
|---|---|
| Active Ingredient | 5.0 mg |
| Corn Oil | 1.0 mL |

EXAMPLE 17

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 18

A topical preparation is prepared having the following composition:

| Ingredients | grams |
|---|---|
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 19

Sustained Release Composition

| Ingredient | Weight Range (%) | Preferred Range (%) | Most Preferred Range (%) |
|---|---|---|---|
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base, which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably, the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 20

$A_{2B}$ Adenosine Receptor Assays

Methods

Radioligand binding. Human $A_{2B}$ adenosine receptor cDNA was stably transfected into Hek-293 cells. Monolayer of Hek-A2B cells were washed with PBS once and harvested in a buffer containing 10 mM HEPES (pH7.4), 10 mM EDTA and protease inhibitors. These cells were homogenized in polytron for 1 minute at setting 4 and centrifuged at 29000 g for 15 minutes at 4° C. The cell pellets were washed once with a buffer containing 10 mM HEPES (pH7.4), 1 mM EDTA and protease inhibitors, and were resuspended in the same buffer supplemented with 10% sucrose. Frozen aliquots were kept at −80° C. Competition assays were started by mixing 10 nM 3H-ZM214385 (Tocris Cookson) with various concentrations of test compounds and 25 ug membrane proteins in TE buffer (50 mM Tris and 1 mM EDTA) supplemented with 1 U/ml adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 10 uM ZM214385. $B_{max}$ and $K_D$ values were calculated using GraphPad software.

cAMP measurements. Monolayer of Hek-A2B cells were collected in PBS containing 5 mM EDTA. Cells were washed once with DMEM and resuspended in DMEM containing 1 U/ml adenosine deaminase at a density of 300,000 cells/ml. 100 ul of the cell suspension was mixed with 25 ul test compounds and the reaction was kept at 37° C. for 10 minutes. At the end of 10 minutes, 125 ul 0.2N HCl was added to stop the reaction. Cells were centrifuged for 10 minutes at 1000 rpm. 100 ul of the supernatant was removed and acetylated. The concentration of cAMP in the supernatants was measured using the direct cAMP assay from Assay Design.

The compounds of Formula I were shown to be $A_{2B}$-antagonists by the above tests.

EXAMPLE 21

$A_{2B}$ Adenosine Receptor Assays

The human $A_{2B}$ receptor cDNA is subcloned into the expression plasmid pDoubleTrouble as described in Robeva, A. et al., Biochem-Pharmacol., 51, 545–555 (1996). The plasmid is amplified in competent JM109 cells and plasmid DNA isolated using Wizard Megaprep columns (Promega Corporation, Madison, Wis.). $A_{2B}$ adenosine receptors are introduced into HEK-293 cells by means of Lipofectin as described in Feigner, P. L. et al., Proc-Natl Acarl Sci-TJSA, 84, 7413–7417 (1987).

Transfected HEK cells are grown under 5% $CO_2$/95% $O_2$ humidified atmosphere at a temperature of 37° C. Colonies are selected by growth of cells in 0.6 mg/mL G418. Transfected cells are maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells are cultured in 10 cm diameter round plates and subcultured when grown confluent (approximately after 72 hours).

Radioligand Binding Studies.

At $A_{2B}$ Receptors:

Confluent monolayers of HEK-$A_{2B}$ cells are washed with PBS followed by ice cold Buffer A (10 mM HEPES, 10 mM EDTA, pH 7.4) with protease inhibitors (10 μg/mL benzamidine, 100 μM phenylmethanesulfonyl fluoride, and 2 g/mL of each aprotinin, pepstatin and leupeptin). The cells are homogenized in a Polytron (Brinkmann) for 20 seconds, centrifuged at 30,000×g, and the pellets washed twice with buffer HE (10 mM HEPES, 1 mM EDTA, pH 7.4 with protease inhibitors). The final pellet is resuspended in buffer HE, supplemented with 10% sucrose and frozen in aliquots at −80° C. For binding assays membranes are thawed and diluted 5–10 fold with HE to a final protein concentration of approximately 1 mg/mL. To determine protein concentrations, membranes, and bovine serum albumin standards are dissolved in 0.2% NaOH/0.01% SDS and protein determined using fluorescamine fluorescence. Stowell, C. P. et al., *Anal. Biochem.*, 85., 572–580 (1978).

Saturation binding assays for human $A_{2B}$ adenosine receptors are performed with [$^3$H]ZM214,385 Competition assays are performed by measuring the amount of $^3$H-ZM214385 (tritiated 4-(2-[7-amino-2-(2furyl)[1,2,4]-triazolo[2,33-a][1,3,5]triazin-5-ylamino]ethyl)phenol) (17 Ci/mmol, Tocris Cookson, Bristol UK) (Ji, X. et al., *Drug Design Discov.*, 16, 216–226 (1999)), an adenosine A2 antagonist, displaced by the $A_{2B}$ antagonists.

Briefly, membranes (25 µg) are resuspended in TE buffer (50 mM Tris and 1 mM EDTA) supplemented with 1 U/ml adenosine deaminase and mixed with 10 nM $^3$H-ZM214385 with or without various concentrations of test compounds. The assay mixture is incubated for 90 minutes and then the reaction stopped by filtration through a Packard Harvester. The filters are washed four times with ice-cold TM buffer (10 mM Tris, 1 mM MgCl$_2$, pH 7.4). Non specific binding is determined in the presence of 10 uM ZM214385. The effect of the $A_{2B}$ antagonists on the binding of the $^{125I}$-ZM214385 to the membranes is determined by counting the radioactivity in a scintillation counter. The $B_{max}$ and $K_D$ values are calculated using GraphPad software.

K, values for different compounds are derived from IC$_{50}$ values as described. Linden, J., *J. Cycl. Nucl. Res.*, 8.,163–172 (1982). Data from replicate experiments are tabulated as means: ±SEM.

At Other Adenosine Receptors:

[$^3$H]CPX. Bruns, R. F. et al., *Naunyn-Schmiedeberg's Arch. Pharmacol.*, 335, 59–63 (1987). $^{125}$I-ZM241385 and $^{125}$I-ABA are utilized in radioligand binding assays to membranes derived from HEK-293 cells expressing recombinant human A$_1$, A$_{2A}$ and A$_3$ ARs, respectively. Binding of [$^3$H]R—N$^6$-phenylisopropyladenosine. Schwabe, U. et al., *Naunyn-Schmiedeberg's Arch. Pharmacol.*, 313,179–187 (1980). ([$^3$H]R-PIA, Amersham, Chicago, Ill.) to A$_1$ receptors from rat cerebral cortical membranes and of [$^3$H]CGS 21680. Jarvis, M. F. et al., *J-Pharmacol Exp. Therap.*, 251, 888–893 (1989). (Dupont NEN, Boston, Mass.) to A$_{2A}$ receptors from rat striatal membranes is performed as described. Adenosine deaminase (3 units/mL) is present during the preparation of the brain membranes, in a preincubation of 30 min at 30° C., and during the incubation with the radioligands. All non-radioactive compounds are initially dissolved in DMSO, and diluted with buffer to the final concentration, where the amount of DMSO never exceeds 2%. Incubations are terminated by rapid filtration over Whatman GF/B filters, using a Brandell cell harvester (Brandell, Gaithersburg, Md.). The tubes are rinsed three times with 3 mL buffer each.

At least six different concentrations of competitor, spanning 3 orders of magnitude adjusted appropriately for the IC$_{50}$ of each compound, are used.

IC$_{50}$ values, calculated with the nonlinear regression method implemented in (Graph-Pad Prism, San Diego, Calif.), are converted to apparent~values as described. Linden, J., *J. Cycl Nucl. Res.*, 8.:163–172 (1982). Hill coefficients of the tested compounds are in the range of 0.8 to 1.1.

EXAMPLE 22

Cyclic AMP Accumulation

Cyclic AMP generation is performed in DMEM/HEPES buffer (DMEM containing 50 mM HEPES, pH 7.4, 37° C.). Each well of cells is washed twice with DMEM/HEPES buffer, and then 100 µL adenosine deaminase (final concentration 10 IU/mL) and 100 µL of solutions of N-ethylcarboxyamido-adenosine (NECA), an adenosine receptor agonist, which stimulates cAMP synthesis, is added. Then, 50 µL of the test compound (appropriate concentration) or buffer are added to some of the wells. After a 10 minute incubation at 37° C. in an atmosphere of 5% CO$_2$ in air the cells are harvested and centrifuged for 10 minutes at 1000 rpm. 100 µl of the supernatant is removed and acetylated. The effect of the A$_{2B}$ antagonist on the NECA-stimulation of cAMP is measured using the direct cAMP assay from Assay Design.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound of the formula:

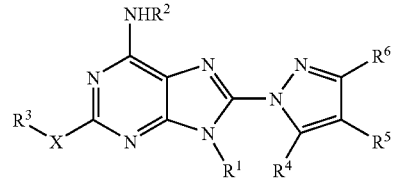

Formula I wherein:

R$^1$ is optionally substituted alkyl;

R$^2$ is hydrogen, acyl, or optionally substituted alkyl;

R$^3$ is —Y-Z$^1$, in which Y is a covalent bond or optionally substituted alkylene, and Z$^1$ is optionally substituted phenyl;

R$^4$ and R$^6$ are independently hydrogen, optionally substituted aryl, or optionally substituted alkyl;

R$^5$ is hydrogen, optionally substituted alkyl, halo, CF$_3$, nitro, cyano, optionally substituted alkoxy, optionally substituted thioalkoxy, optionally substituted amino, optionally substituted sulfoxide, optionally substituted sulfone, optionally substituted sulfonamide, optionally substituted acylamino, optionally substituted alkenyl, optionally substituted alkynyl, optionally substituted aryl, optionally substituted heteroaryl, or optionally substituted heterocyclyl; and X is NH—, or a pharmaceutically acceptable salt, ester, or prodrug thereof.

2. A method of antagonizing an $A_{2B}$ adenosine receptors in a mammal, comprising administering to a mammal in need thereof a therapeutically effective dose of a compound of claim 1.

3. The method of claim 2, wherein the $A_{2B}$ adenosine receptors are antagonized in order to treat a disease state chosen from diabetic retinopathy and asthma.

4. The method of claim 2, wherein the $A_{2B}$ adenosine receptors are antagonized in order to treat an inflammatory gastrointestinal tract disorder.

5. The method of claim 4, wherein the inflammatory gastrointestinal tract disorder is diarrhea.

6. A pharmaceutical composition comprising at least one pharmaceutically acceptable excipient and a therapeutically effective amount of a compound of claim 1.

7. The compound of claim 1, wherein $R^1$ is ethyl, propyl, or 3,3,3-trifluoropropyl.

8. The compound of claim 7, wherein Y is optionally substituted methylene, ethylene or propylene.

9. The compound of claim 8, wherein $R^2$ is hydrogen.

10. The compound of claim 9, wherein $R^4$, $R^5$, and $R^6$ are all hydrogen.

11. The compound of claim 10, selected from the group consisting of
   $N^2$ benzyl-8-(pyrazol-1-yl)-9-ethyl-9H-purine-2,6-diamine
   $N^2$ (3-phenylpropyl)-9-propyl-8-(pyrazol-1-yl)-9H-purine-2,6-diamine;
   $N^2$ (2-(2-fluorophenyl)ethyl)-9-propyl-8-(pyrazol-1-yl)-9H-purine-2,6-diamine;
   $N^2$ phenylethyl-8-(pyrazol-1-yl)-9-(3,3,3-trifluoropropyl)-9H-purine-2,6-diamine;
   $N^2$ (2-phenylpropyl)-9-propyl-8-(pyrazol-1-yl)-9H-purine-2,6-diamine, R and S isomers;
   $N^2$ (2-(4-chlorophenyl)ethyl)-9-propyl-8-(pyrazol-1-yl)-9H-purine-2,6-diamine;
   $N^2$ (2-(2-chlorophenyl)ethyl)-9-propyl-8-(pyrazol-1-yl)-9H-purine-2,6-diamine;
   $N^2$ (2-(2,5-dimethoxyphenyl)ethyl)-9-propyl-8-(pyrazol-1-yl)-9H-purine-2,6-diamine;
   $N^2$ (2-(2,4-dichlorophenyl)ethyl)-9-propyl-8-(pyrazol-1-yl)-9H-purine-2,6-diamine;
   $N^2$ (2-(2-methoxyphenyl)ethyl)-9-propyl-8-(pyrazol-1-yl)-9H-purine-2,6-diamine;
   $N^2$ ((2-hydroxymethyl)benzyl)-9-propyl-8-(pyrazol-1-yl)-9H-purine-2,6-diamine;
   $N^2$ (4-aminomethylbenzyl)-9-propyl-8-(pyrazol-1-yl)-9H-purine-2,6-diamine;
   $N^2$ (3-aminomethylbenzyl)-9-propyl-8-(pyrazol-1-yl)-9H-purine-2,6-diamine;
   $N^2$ (2-aminomethylbenzyl)-9-propyl-8-(pyrazol-1-yl)-9H-purine-2,6-diamine;
   $N^2$ ((4-hydroxymethyl)benzyl)-9-propyl-8-(pyrazol-1-yl)-9H-purine-2,6-diamine;
   $N^2$ ((3-hydroxymethyl)benzyl)-9-propyl-8-(pyrazol-1-yl)-9H-purine-2,6-diamine;
   $N^2$ (2-(4-fluorophenyl)ethyl)-9-propyl-8-(pyrazol-1-yl)-9H-purine-2,6-diamine; and
   $N^2$ (2-(3-fluorophenyl)ethyl)-9-propyl-8-(pyrazol-1-yl)-9H-purine-2,6-diamine.

12. The compound of claim 9, wherein $R^4$ and $R^6$ are hydrogen and $R^5$ is halogen, optionally substituted lower alkyl, optionally substituted alkenyl, or optionally substituted aryl.

13. The compound of claim 12, wherein $R^5$ optionally substituted lower alkyl.

14. The compound of claim 13, selected from the group consisting of
   $N^2$ (1R-1-phenylethyl)-9-ethyl-8-(4-methylpyrazol-1-yl)-9H-purine-2,6-diamine;
   $N^2$ benzyl-9-ethyl-8-(4-methylpyrazol-1-yl)-9H-purine-2,6-diamine;
   $N^2$ ((1-phenyl)ethyl)-9-propyl-8-(4-methylpyrazol-1-yl)-9H-purine-2,6-diamine;
   $N^2$ benzyl-8-(4-vinylpyrazol-1-yl)-9-ethyl-9H-purine-2,6-diamine; and
   $N^2$ benzyl-8-[4-allylpyrazol-1-yl]-9-ethyl-9H-purine-2,6-diamine.

15. The compound of claim 12, wherein $R^5$ is optionally substituted aryl.

16. The compound of claim 15, wherein $R^5$ is optionally substituted phenyl.

17. The compound of claim 16, selected from the group consisting of
   N2-benzyl-9-ethyl-8-(4-phenyl-1H-pyrazol-1-yl)-9H-purine-2,6-diamine;
   $N^2$ benzyl-8-[4-(4-methylphenyl)pyrazol-1-yl]-9-ethyl-9H-purine-2,6-diamine;
   $N^2$ benzyl-8-[4-(4-fluorophenyl)pyrazol-1-yl]-9-ethyl-9H-purine-2,6-diamine;
   $N^2$ benzyl-8-[4-(4-methoxyphenyl)pyrazol-1-yl]-9-ethyl-9H-purine-2,6-diamine; and
   $N^2$ benzyl-8-[4-(3-trifluoromethylphenyl)pyrazol-1-yl]-9-ethyl-9H-purine-2,6-diamine.

18. The compound of claim 12, wherein $R^5$ is halogen.

19. The compound of claim 18, wherein $R^1$ is ethyl, $R^2$ is hydrogen, Y is methylene and $Z^1$ is phenyl so that $R^3$ is benzyl, $R^4$ and $R^6$ are hydrogen and $R^5$ is iodine, namely, $N^2$ benzyl-9-ethyl-8-(4-iodopyrazol-1-yl)-9H-purine-2,6-diamine.

20. The compound of claim 8, wherein $R^2$ is optionally substituted lower alkyl.

21. The compound of claim 20, wherein $R^1$ is propyl, $R^2$ is isobutyl, Y is ethylene and $Z^1$ is phenyl so that $R^3$ is phenylethyl, and $R^4$, $R^5$, and $R^6$ are all hydrogen, namely $N^2$ 2-phenylethyl-$N^6$-isobutyl-9-propyl-8-(pyrazol-1-yl)-9H-purine-2,6-diamine.

22. The compound of claim 8, wherein $R^2$ is acyl of formula —C(O)R, in which R is hydrogen, optionally substituted alkyl, optionally substituted cycloalkyl, optionally substituted heterocyclyl, optionally substituted aryl, or optionally substituted heteroaryl.

23. The compound of claim 22, wherein R is optionally substituted lower alkyl.

24. The compound of claim 23, wherein $R^4$, $R^5$, and $R^6$ are all hydrogen.

25. The compound of claim 24, selected from the group consisting of
   $N^2$ phenylethyl-$N^6$-(2-methylbutanoyl)-8-(pyrazol-1-yl)-9-(prop-1-yl)-9H-purine-2,6-diamine;
   $N^2$ phenylethyl-$N^6$-(2-ethylbutanoyl)-8-(pyrazol-1-yl)-9-(prop-1-yl)-9H-purine-2,6-diamine;
   $N^2$ phenylethyl-$N^6$-(2,2,-diimethylpropanoyl)-8-(pyrazol-1-yl)-9-(prop-1-yl)-9H-purine-2,6-diamine;
   $N^2$ phenylethyl-$N^6$-(2,2-diphenylacetyl)-8-(pyrazol-1-yl)-9-(prop-1-yl)-9H-purine-2,6-diamine;
   $N^2$ phenylethyl-$N^6$-(2-methylpropanoyl)-8-(pyrazol-1-yl)-9-(prop-1-yl)-9H-purine-2,6-diamine;
   $N^2$ benzyl-$N^6$-(2,2-dimethylpropionyl) 8-(pyrazol-1-yl)-9-ethyl-9H-purine-2,6-diamine
   $N^2$ benzyl-$N^6$-(3-ethoxycarbonylpropionyl) 8-(pyrazol-1-yl)-9-ethyl-9H-purine-2,6-diamine;

N² benzyl-N⁶-(2-methoxyacetyl) 8-(pyrazol-1-yl)-9-ethyl-9H-purine-2,6-diamine);

N² phenylethyl-N⁶-(2-n-propylpentanoyl)-8-(pyrazol-1-yl)-9-(prop-1-yl)-9H-purine-2,6-diamine; and N² phenylethyl-N⁶-(2-methylpentanoyl)-8-(pyrazol-1-yl)-9-(prop-1-yl)-9H-purine-2,6-diamine.

26. The compound of claim 23, wherein $R^4$ and $R^6$ are hydrogen and $R^5$ is halogen, optionally substituted lower alkyl, or optionally substituted aryl.

27. The compound of claim 26, wherein $R^1$ is ethyl, $R^2$ is 2,2-dimethylpropionyl, Y is methylene and $Z^1$ is phenyl so that $R^3$ is benzyl, $R^4$ and $R^6$ are hydrogen, and $R^5$ is 4-methylphenyl, namely N²benzyl-N⁶-(2,2-dimethylpropionyl) 8-[4-(4-methylphenyl)-pyrazol-1-yl]-9-ethyl-9H-purine-2,6-diamine.

28. The compound of claim 26, wherein $R^1$ is ethyl, $R^2$ is 2,2-dimethylpropionyl, Y is methylene and $Z^1$ is phenyl so that $R^3$ is benzyl, and $R^4$ and $R^6$ are hydrogen, and $R^5$ is methyl, ,namely N² benzyl-N⁶-(2,2-dimethylpropionyl) 8-(4-methylpyrazol-1-yl)-9-ethyl-9H-purine-2,6-diamine.

29. The compound of claim 22, wherein R is optionally substituted aryl.

30. The compound of claim 29, wherein $R^4$, $R^5$, and $R^6$ are all hydrogen.

31. The compound of claim 30, selected from the group consisting of

N² phenylethyl-N⁶-(benzoyl)-8-(pyrazol-1-yl)-9-(prop-1-yl)-9H-purine-2,6-diamine;

N² phenylethyl-N⁶-(4-t-butylbenzoyl)-8-(pyrazol-1-yl)-9-(prop-1-yl)-9H-purine-2,6-diamine;

N² phenylethyl-N⁶-(3,4-difluorobenzoyl)-8-(pyrazol-1-yl)-9-(prop-1-yl)-9H-purine-2,6-diamine;

N² phenylethyl-N⁶-(3-trifluoromethylbenzoyl)-8-(pyrazol-1-yl)-9-(prop-1-yl)-9H-purine-2,6-diamine;

N² phenylethyl-N⁶-(3,5-dimethoxybenzoyl)-8-(pyrazol-1-yl)-9-(prop-1-yl)-9H-purine-2,6-diamine;

N² phenylethyl-N⁶-(4-cyanobenzoyl)-8-(pyrazol-1-yl)-9-(prop-1-yl)-9H-purine-2,6-diamine; and N² phenylethyl-N⁶-(4-phenylbenzoyl)-8-(pyrazol-1-yl)-9-(prop-1-yl)-9H-purine-2,6-diamine.

32. The compound of claim 22, wherein R is optionally substituted cycloalkyl.

33. The compound of claim 32, wherein $R^4$, $R^5$, and $R^6$ are all hydrogen.

34. The compound of claim 33, selected from the group consisting of

;(5,6-dihydroxybicyclo[2.2.1]hept-2-yl)-N-{2-[(2-phenylethyl)amino]-9-propyl-8-pyrazolylpurin-6-yl}carboxamide;

N² phenylethyl-N⁶-(cyclopropanoyl)-8-(pyrazol-1-yl)-9-(prop-1-yl)-9H-purine-2,6-diamine;

N² phenylethyl-N⁶-(cyclobutanoyl)-8-(pyrazol-1-yl)-9-(prop-1-yl)-9H-purine-2,6-diamine;

N² phenylethyl-N⁶-(cyclopentanoyl)-8-(pyrazol-1-yl)-9-(prop-1-yl)-9H-purine-2,6-diamine; and N² phenylethyl-N⁶-(cyclohexanoyl)-8-(pyrazol-1-yl)-9-(prop-1-yl)-9H-purine-2,6-diamine.

35. The compound of claim 22, wherein $R^1$ is propyl, $R^2$ is 3,4-methylenedioxybenzoyl, Y is ethylene and $Z^1$ is phenyl so that $R^3$ is phenylethyl, and $R^4$, $R^5$, and $R^6$ are hydrogen, namely N² phenylethyl-N⁶-(3,4-methylenedioxybenzoyl)-8-(pyrazol-1-yl)-9-(prop-1-yl)-9H-purine-2,6-diamine.

36. The compound of claim 9, wherein $R^1$ is ethyl, $R^2$ is hydrogen, Y is methylene and $Z^1$ is is phenyl so that $R^3$ is benzyl, $R^4$ and $R^5$ are hydrogen, and $R^6$ is 4-methylphenyl, namely N² benzyl-9-ethyl-8-[3-(4-methylphenyl)pyrazol-1-yl]-9H-purine-2,6-diamine.

37. The compound of claim 9, wherein $R^1$ is ethyl, $R^2$ is hydrogen, Y is methylene and $Z^1$ is phenyl so that $R^3$ is benzyl, $R^4$ and $R^6$ are methyl, and $R^5$ is hydrogen, namely N²-benzyl-9-ethyl-8-(3,5-dimethyl-1H-pyrazol-1-yl)-4H-purine-2,6-diamine.

38. The compound of claim 9, wherein $R^1$ is ethyl, $R^2$ is hydrogen, Y is methylene and Z1 is phenyl so that $R^3$ is benzyl, $R^4$ and $R^5$ are hydrogen, and $R^6$ is 4-methylphenyl, namely N² benzyl-9-ethyl-8-[3-(4-methylphenyl)pyrazol-1-yl]-9H-purine-2,6-diamine.

* * * * *